United States Patent [19]

Hara et al.

[11] Patent Number: 5,134,125
[45] Date of Patent: Jul. 28, 1992

[54] NUTRIENT COMPOSITION

[75] Inventors: Takahiro Hara, Machida, Japan; Tadayasu Furukawa, Chesterfield, Mo.

[73] Assignee: Kyowa Hakko Kogyo Co., Ltd., Tokyo, Japan

[21] Appl. No.: 613,687

[22] PCT Filed: May 22, 1990

[86] PCT No.: PCT/JP90/00651
§ 371 Date: Oct. 19, 1990
§ 102(e) Date: Oct. 19, 1990

[87] PCT Pub. No.: WO90/11024
PCT Pub. Date: Oct. 4, 1990

[30] Foreign Application Priority Data

Mar. 28, 1989 [JP] Japan ..................... 1-75778

[51] Int. Cl.$^5$ .................. A61K 37/02; C07K 5/06
[52] U.S. Cl. ............................ 514/19; 426/656
[58] Field of Search ..................... 514/19; 426/656

[56] References Cited

U.S. PATENT DOCUMENTS 4,024,286 5/1977 Cornelius et al. .
4,340,592 7/1982 Adibi .

FOREIGN PATENT DOCUMENTS 0044032 1/1982 European Pat. Off. .
0087750 6/1985 European Pat. Off. .
882163 11/1961 United Kingdom .

OTHER PUBLICATIONS

Stehle et al. The Lancet Feb. 4, 1989 pp. 231-233.
Hübl et al. Metabolism, vol. 38, No. 8 Suppl 1 (Aug.) 1989 pp. 59-62.
Taniguchi et al. JBC, vol. 253, No. 6 (Mar. 1978) pp. 1799-1806.
Albers et al. Clinical Science (1988) 75 pp. 463-468.

Primary Examiner—Howard E. Schain
Assistant Examiner—Choon P. Koh
Attorney, Agent, or Firm—Antonelli, Terry, Stout & Kraus

[57] ABSTRACT

The present invention relates to nutrient compositions for mammals comprising L-glutamyl-L-glutamine.

5 Claims, 1 Drawing Sheet

NUTRIENT COMPOSITION

TECHNICAL FIELD

The present invention relates to nutrient compositions for mammals, and more particularly, to nutrient compositions comprising L-glutamyl-L-glutamine.

BACKGROUND ART

Humans and other mammals require daily intake of proteins for their life activities. Proteins are converted into amino acids in the digestive tract and utilized *in vivo* for growth, reproduction, assimilation, etc.

However, it is often difficult to take nutrients from ordinary foods under conditions such as postoperative lowering of function of the digestive tract and malnutrition due to apastia, starvation, etc., where nutrient supplementation is required. In addition, during or after hard physical labor or exercise, etc., metabolic function is enhanced and nitrogen is seriously lost by perspiration, and thus nutrient supplementation is necessary. In such cases, large quantities of proteins or amino acids must be taken in a readily absorbable form with minimized burden on the digestive tract.

Conventional methods for nutrient supplementation include intravenous injection and instillation of amino acids, and oral or intra-intestinal administration of nutrient compositions containing proteins of good quality such as meat extract, casein and albumen, amino acids, peptides, etc.

However, the use of some kinds of amino acids is limited because of their poor solubility, instability, etc. In particular, it is pointed out that supplementation of L-glutamine is necessary for a patient in postoperative catabolic condition since L-glutamine in the muscle of such a patient seriously decreases; but L-glutamine itself cannot be contained in known nutrient compositions which are sterilized by heating in the preparation process since it is unstable in solution and also has a poor stability to heat.

In order to supply L-glutamine which is unstable in solution as a nutrient composition for mammals, there have been developed nutrient compositions comprising L-glutamine in the form of α-L-aspartyl-L-glutamine (Japanese Published Unexamined Pat. Application No. 151156/1987), nutrient compositions comprising L-glutamine in the form of glycyl-L-glutamine (Japanese Published Unexamined Pat. Application No. 140923/1981), etc., by converting L-glutamine into a dipeptide.

Further, there is a report on the behavior of L-alanyl-L-glutamine in plasma and the uptake thereof by organs in Clinical Science, 75, 463 (1988).

In the nutrient compositions comprising α-L-aspartyl-L-glutamine or glycyl-L-glutamine, the stability of L-glutamine is considerably improved, but still they should be improved in many points such as stability under sterilizing conditions, absorption *in vivo* and utilization efficiency *in vivo*.

Further, when nutrient compositions comprising L-glutamine-containing dipeptides instead of L-glutamine are taken, these dipeptides must be hydrolyzed to amino acids *in vivo*. Conventionally used dipeptides were improved in stability of L-glutamine to heat, etc. but are not satisfactory in absorption *in vivo* and utilization efficiency *in vivo*.

DISCLOSURE OF THE INVENTION

The present inventors have found that by the use of L-glutamyl-L-glutamine instead of L-glutamine-containing dipeptides used heretofore, absorption, utilization efficiency, etc. of dipeptide *in vivo* can be improved as compared with conventional nutrient compositions, and have accomplished the present invention.

The present invention provides nutrient compositions comprising L-glutamyl-L-glutamine.

The present invention is described in detail below.

The nutrient compositions comprising L-glutamyl-L-glutamine are used mainly as nutrient compositions for oral or intra-intestinal administration.

In the case of oral administration, nutrient additives such as readily digestible carbohydrates, fats, vitamins and minerals may be added to the compositions to adjust the nutrient balance. Further, tasting and flavoring agents such as pseudo-tasting agents, sweeteners, flavors and dyes, appearance-improving agents, etc. may also be added to improve flavor of the compositions for oral administration. Specific examples of the nutrient additives include starch, dextrin, glucose, maltose, lactose, skimmed milk, egg yolk powder, egg yolk oil, malt extract, medium chain fatty acid, vitamin A, thiamine, riboflavin, pyridoxine, niacin, pantothenic acid, cyanocobalamin, L-ascorbic acid, α-tocophenol, sodium chloride, potassium chloride, calcium chloride, and iron lactate.

The components described above are blended, mixed with water and dispersed, and the resulting composition as drink or paste is sealed in a moistureproof bag, bottle, can, etc. and then sterilized by heating prior to storage, distribution and use. Alternatively, these components may be thoroughly mixed, and the mixture may be stored and distributed in a powdery state and mixed with water and dispersed just before use. In these procedures, treatments such as cooking with heating and sterilization can be freely carried out since L-glutamyl-L-glutamine is highly stable to heat and stable in solution over long periods of time.

A preferred example of the nutrient composition for supplementing glutamine is a composition comprising 0.0005 to 30 wt% of L-glutamyl-L-glutamine together with amino acids or protein hydrolyzates, the aforesaid nutrient additives and the like (e.g., an amino acid infusion, a nutrient preparation for oral nutrient supplementation, and a jelly-like nutrient preparation).

The amino acid infusion comprising L-glutamyl-L-glutamine has the following composition, for example, wherein unit is mg/dl.

| L-Isoleucine | 160–1070 |
| --- | --- |
| L-Leucine | 180–1720 |
| L-Lysine hydrochloride | 180–2400 |
| L-Phenylalanine | 130–1400 |
| L-Methionine | 50–1200 |
| L-Threonine | 80–720 |
| L-Tryptophan | 30–350 |
| L-Valine | 70–1130 |
| L-Arginine hydrochloride | 120–1500 |
| L-Histidine hydrochloride | 50–900 |
| Glycine | 200–2500 |
| L-Alanine | 70–1130 |
| Sodium L-aspartate | 0–1300 |
| L-Cysteine | 0–150 |
| Sodium L-glutamate | 0–1300 |
| L-Glutamyl-L-glutamine | 1–5000 |
| L-Proline | 90–1080 |
| L-Serine | 60–820 |

-continued

| | |
|---|---|
| L-Tyrosine | 3–90 |

L-Glutamyl-L-glutamine is of two types, α and γ, and the γ type is preferably used.

γ-L-glutamyl-L-glutamine has a higher stability to heat than L-glutamine. In addition, it is assumed that γ-L-glutamyl-L-glutamine is efficiently utilized in vivo, since it is an effective substrate for γ- glutamyl transferase and γ- glutamyl cyclotransferase [J. Biol. Chem., vol. 253, No. 6, p. 1799–1806 (1978)].

When L-glutamyl-L-glutamine is used in the nutrient composition, it must be hydrolyzed to amino acids in vivo.

It is reported by Matthews, et al. and Adibi, et al. that the rate of absorption of amino acids from di- and tripeptides is faster than that from an amino acid mixture having the same composition [Gut, vol. 9, p. 425 (1968), Clinical Research, vol. 16, p. 446 (1968)]. Further, as described above, γ-glutamyl transferase and γ-glutamyl cyclotransferase are present in vivo and γ-L-glutamyl-L-glutamine is their effective substrate. Therefore, γ-L-glutamyl-L-glutamine is considered to be readily hydrolyzed in vivo and absorbed in the body. It is thus considered that γ-L-glutamyl-L-glutamine is usable also as a nutrient supplementation agent having an immediate effect for a person in physiological or pathological state where quick supplementation of nutrients is required, for example, when physical strength is lost after hard physical labor, exercise, etc. and when quick recovery of physical strength is required after a surgical operation, etc.

The change in concentration of γ-L-glutamyl-L-glutamine and various dipeptides containing L-glutamine in human and mouse plasma (model system), the stability of them in the presence of γ-glutamyl transferase (γ-GTP), and the change in concentration in blood and influence on the glutamine level in organ of the dipeptides administered to mice are described below.

(1) Hydrolysis of dipeptides in human plasma

Each of the dipeptides shown in Table 1 below was added to 0.75 ml of plasma collected and prepared from human to give a concentration of 10 mM, followed by reaction at 37° C. for 30 minutes. The residual rates of the dipeptides after completion of the reaction are shown in Table 1.

TABLE 1

| Dipeptide | Residual Rate (%) |
|---|---|
| γ-L-Glutamyl-L-glutamine | 99 |
| L-Alanyl-L-glutamine | 74 |
| Glycyl-L-glutamine | 84 |
| L-Aspartyl-L-glutamine | 58 |

Compared with the dipeptides conventionally used, γ-L-glutamyl-L-glutamine was substantially free of hydrolysis in human plasma and showed high stability.

(2) Hydrolysis of dipeptides by γ-GTP (γ-glutamyl transferase)

After each of the dipeptides shown in Table 1 above was dissolved in Tris-HCl buffer (50 mM, pH 7.0) in a concentration of 5 mM, γ-GTP prepared from swine kidney was added to the solution, followed by reaction at 37° C. for 120 minutes. γ-L-Glutamyl-L-glutamine was almost completely hydrolyzed, whereas the other dipeptides were not hydrolyzed at all. (3) Hydrolysis of dipeptides in mouse plasma Each of the dipeptides shown in Table 2 below was added to 0.05 ml of plasma collected and prepared from C3H/He mice (6 weeks of age, male, weighing 20 g) to give a concentration of 3.13 mM, followed by reaction at 37° C. for 2, 5, 10 and 20 minutes. The residual rates of the dipeptides after completion of the reaction are shown in Table 2. Five mice were used for each test group, and the results are shown by the mean value.

TABLE 2

| Dipeptide | Residual Rate (%) | | | | |
|---|---|---|---|---|---|
| | 2 | 5 | 10 | 20 | (minutes) |
| γ-L-Glutamyl-L-glutamine | 100 | 100 | 100 | 100 | |
| L-Alanyl-L-glutamine | 87 | 62 | 24 | 11 | |

Compared with the dipeptide conventionally used, γ-L-glutamyl-L-glutamine was not hydrolyzed at all in mouse plasma and showed high stability.

(4) Change in concentration in blood of dipeptides administered to mice

γ-L-Glutamyl-L-glutamine and L-alanyl-L-glutamine were respectively administered to C3H/He mice (6 weeks of age, male, weighing 20 g) through the tail vein at a dose of 250 μmoles/kg body weight, and blood was collected intermittently. The change in concentration of the dipeptides and glutamine in the blood with the passage of time is shown in FIG. 1. Five mice were used for each test group, and the results are shown by the mean ±SEM.

L-Alanyl-L-glutamine disappeared extremely rapidly after the administration and simultaneously rapid release of glutamine into the blood was observed. On the other hand, in the groups which received γ-L-glutamyl-L-glutamine, the disappearance of the dipeptide and the appearance of glutamine were slow. It was thus recognized that there was a great difference in change in concentration of the two dipeptides in blood.

(5) Influence of administered dipeptides on renal glutamine level

γ-L-Glutamine-L-glutamine and L-alany-L-glutamine were respectively administered to C3H/He mice (6 weeks of age, male, weighing 20 g) through the tail vein at a dose of 250 γmoles/kg body weight, and after 20 minutes, the kidneys were excised. The glutamine level in the organ was compared to that prior to the administration of the dipeptides. The results are shown in Table 3. Five mice were used for each test group, and the results are shown by the mean ±SEM.

The groups which received γ-L-glutamyl-L-glutamine showed a significantly high renal glutamine level, and this suggests uptake of the dipeptide by the kidney and effective utilization thereof in the organ.

TABLE 3

| Dipeptide | Concentration of Glutamine (μmole/g wet weight) |
|---|---|
| Prior to administration | 1.07 ± 0.08 |
| γ-L-Glutamyl-L-glutamine | 1.57 ± 0.12 |
| L-Alanyl-L-glutamine | 1.14 ± 0.09 |

Thus, γ-L-glutamyl-L-glutamine is characterized in that it is little hydrolyzed in plasma and is specifically hydrolyzed by γ-GTP, compared with the other dipeptides. γ-GTP is widely distributed in vital tissues such as kidney, small intestine and liver. When γ-L-glutamyl-L-glutamine is administered in blood, it can be utilized in the kidney or liver without being hydrolyzed in blood, in contrast to conventional L-glutamine-containing dipeptides. On the other hand, when γ-L-glutamyl-L-glutamine is orally administered, it is considered that γ-L-glutamyl-L-glutamine is hydrolyzed by γ-GTP in the epithelial cells of the small intestine and can be effectively utilized in the intestine.

L-Glutamine in solution (e.g., 10 mM, pH 6.5) was decomposed by 60% under sterilizing conditions at 110° C. for 60 minutes, for γ-L-glutamyl-L-glutamine was not decomposed at all (Table 4). Further, L-glutamine in solution was decomposed by 29% in storage stability test at 40° C. for 30 days, but γ-L-glutamyl-L-glutamine was not decomposed at all (Table 5). γ-L-Glutamyl-L-glutamine thus showed high stability to heat.

TABLE 4

|  | Residual Rate after Sterilization (%) |
|---|---|
| γ-L-Glutamyl-L-glutamine | 100 |
| L-Glutamine | 40 |

TABLE 5

|  | Residual Rate after Storage at 40° C. for 30 days (%) |
|---|---|
| γ-L-Glutamyl-L-glutamine | 100 |
| L-Glutamine | 71 |

Figure 1:
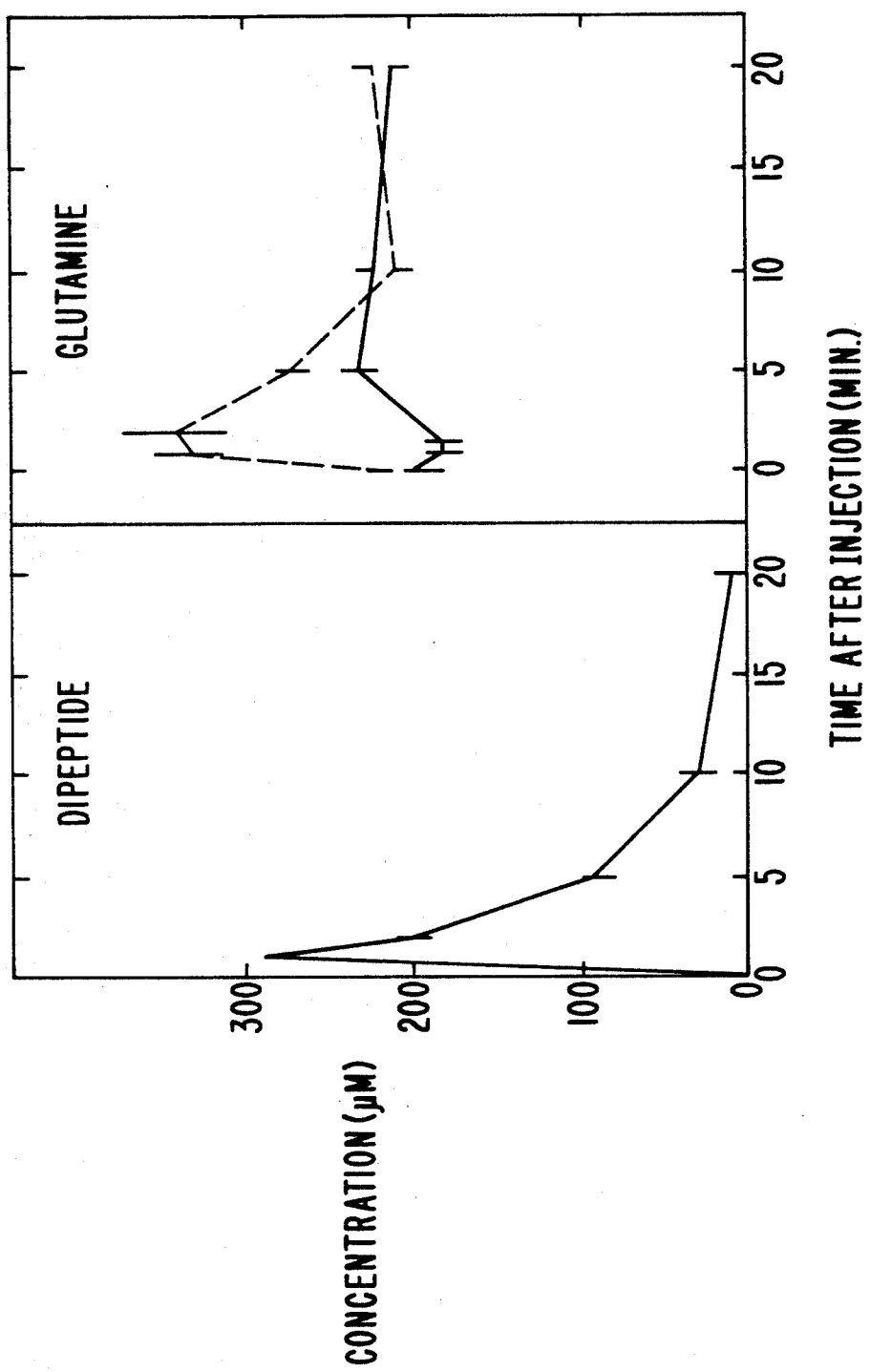
FIG. 1 shows the change with the passage of time in concentration of the dipeptides administered and glutamine in blood which was collected intermittently from the tail vein of mice which received γ-L-glutamyl-L-glutamine or L-alanyl-L-glutamine. The solid line (—²) and the broken line (---) refer to γ-L-glutamyl-L-glutamine and L-alanyl-L-glutamine, respectively.

The present invention is specifically described below by referring to examples.

EXAMPLE 1

To the amino acid composition described below was added 1 liter of distilled water for injection at about 70° C. to dissolve the components. The pH was adjusted to 6.5 with NaOH solution. The solution was filered through a millipore filter and the filtrate was packed in glass bottles in 200 ml portions, followed by blowing with sterile nitrogen gas for 30 seconds. After sealing, the bottles were sterilized by heating at 110° C. for 60 minutes to prepare amino acid infusions.

| L-Isoleucine | 4.6 g |
|---|---|
| L-Leucine | 7.7 g |
| L-Lysine hydrochloride | 5.0 g |
| L-Phenylalanine | 4.3 g |
| L-Methionine | 2.1 g |
| L-Threonine | 2.9 g |
| L-Tryptophan | 1.0 g |
| L-Valine | 4.9 g |
| L-Arginine hydrochloride | 6.1 g |
| L-Histidine hydrochloride | 2.6 g |
| Glycine | 3.4 g |
| L-Alanine | 4.6 g |
| Sodium L-aspartate | 0.3 g |
| L-Cysteine | 0.3 g |
| Sodium L-glutamate | 0.3 g |
| L-Glutamyl-L-glutamine | 3.0 g |
| L-Proline | 3.9 g |
| L-Serine | 2.3 g |

-continued

| L-Tyrosine | 0.3 g |
|---|---|

EXAMPLE 2

| Casein hydrolyzate | 10 g |
|---|---|
| Gelatin | 8 g |
| γ-L-Glutamyl-L-glutamine | 2.5 g |
| Dextrin | 20 g |
| Reduced maltose | 20 g |
| Water | 300 ml |

The above composition was heated at 100° C. for 30 minutes and dispersed. The resultant dispersion was cooled to give a jelly-like nutrient preparation. γ-L-Glutamyl-L-glutamine remained stable under the sterilizing conditions.

EXAMPLE 3

| Casein hydrolyzate | 10 g |
|---|---|
| γ-L-Glutamyl-L-glutamine | 2.5 g |
| Cyclodextrin | 6.3 g |
| Inosinic acid | 0.11 g |
| Citric acid | 16 g |
| Reduced maltose | 6.8 g |
| Orange flavor | 0.07 ml |
| Water | 500 ml |

After the above components were thoroughly mixed and dispersed, the dispersion was sterilized by heating at 110° C. for 60 minutes to give nutrient composition for oral nutrient supplementation. γ-L-Glutamyl-L-glutamine remained stable under the sterilizing conditions.

We claim:

1. A nutirent composition comprising L-glutamyl-L-glutamine.

2. A nutrient composition according to claim 1, wherein said composition contains L-glutamyl-L-glutamine in an amount of 0.0005 to 30 wt%.

3. A nutrient composition according to claim 1 or 2, wherein said nutrient composition is a composition for mammals.

4. A nutrient composition according to claim 3, wherein said nutrient composition is an amino acid infusion.

5. A nutrient composition according to claim 4, wherein said amino acid infusion has the following composition:

| L-Isoleucine | 160–1070 | (mg/dl) |
|---|---|---|
| L-Leucine | 180–1720 | |
| L-Lysine hydrochloride | 180–2400 | |
| L-Phenylalanine | 130–1400 | |
| L-Methionine | 50–1200 | |
| L-Threonine | 80–720 | |
| L-Tryptophan | 30–350 | |
| L-Valine | 70–1130 | |
| L-Arginine hydrochloride | 120–1500 | |
| L-Histidine hydrochloride | 50–900 | |
| Glycine | 200–2500 | |
| L-Alanine | 70–1130 | |
| Sodium L-aspartate | 0–1300 | |
| L-Cysteine | 0–150 | |
| Sodium L-glutamate | 0–1300 | |
| L-Glutamyl-L-glutamine | 1–5000 | |
| L-Proline | 90–1080 | |
| L-Serine | 60–820 | |
| L-Tyrosine | 3–90. | |

* * * * *